(12) United States Patent
Shahidi et al.

(10) Patent No.: US 6,511,418 B2
(45) Date of Patent: Jan. 28, 2003

(54) APPARATUS AND METHOD FOR CALIBRATING AND ENDOSCOPE

(75) Inventors: Ramin Shahidi, San Francisco, CA (US); Marc Epitaux, Sunnyvale, CA (US)

(73) Assignee: The Board of Trustees of The Leland Stanford Junior University, Stanford, CA (US)

( * ) Notice: Subject to any disclaimer, the term of this patent is extended or adjusted under 35 U.S.C. 154(b) by 4 days.

(21) Appl. No.: 09/822,545

(22) Filed: Mar. 30, 2001

(65) Prior Publication Data

US 2002/0010384 A1 Jan. 24, 2002

Related U.S. Application Data

(60) Provisional application No. 60/193,209, filed on Mar. 30, 2000.

(51) Int. Cl.$^7$ .............................. A61B 1/00; G01B 21/00
(52) U.S. Cl. ...................... 600/117; 600/102; 73/1.79
(58) Field of Search .................................. 600/118, 117, 600/109, 424, 102; 356/51, 125, 143, 138, 908, 909; 348/130; 73/1.75, 1.79, 1.81

(56) References Cited

U.S. PATENT DOCUMENTS

| 5,704,897 | A | * | 1/1998 | Truppe ........................ 128/922 |
| 5,820,547 | A | * | 10/1998 | Strobl et al. ................. 348/188 |
| 6,081,336 | A | * | 6/2000 | Messner et al. ....... 250/559.29 |
| 6,306,126 | B1 | * | 10/2001 | Moctezuma .................... 606/1 |
| 6,388,742 | B1 | * | 5/2002 | Duckett ...................... 356/73.1 |

OTHER PUBLICATIONS

Asari, K.V., et al., "Technique of distortion correction in endoscopic images using a polynomial expansion," *Med. Biol. Comput.*, 37:8–12 (1999).

Khadem, R., et al., "Comparative Tracking Error Analysis of Five Different Optical Tracking Systems," *Computer Aided Surgery*, 5:98–107 (2000).

Krotkov, E., et al., "Stereo Ranging with Verging Cameras," *IEEE Transactions on Pattern Analysis and Machine Intelligence*, 12(12):1200–1205 (1990).

Shahidi, R., "Applications of virtual reality in stereotactic procedures: volumetric image navigation via a surgical microscope," Ph.D. Dissertation, Rutgers University, Rutgers, NJ, abstract only (1995).

Tsai, R.Y., "An Efficient and Accurate Camera Calibration Technique for 3D Machine Vision," *Proceedings of IEEE Conference on Computer Vision and Pattern Recognition*, pp. 364–374 (1986).

Viergever, M.A., (ed.), "Image Guidance of Therapy," *IEEE Transactions on Medical Image*, 17(5):669–685 (1998).

Vining, D.J., "Virtual Endoscopy: Is It Reality?" *Radiology*, 200:30–31 (1996).

Weng, J., et al., "Camera Calibration with Distortion Models and Accuracy Evaluation," *IEEE Transactions on Pattern Analysis and Machine Intelligence*, 14(10):965–980 (1992).

\* cited by examiner

*Primary Examiner*—John P. Leubecker
(74) *Attorney, Agent, or Firm*—Perkins Coie LLP

(57) ABSTRACT

An apparatus for use in calibrating lens position and field of view in an endoscope is disclosed. The apparatus includes tracking elements mounted at fixed positions on the endoscope's shaft, a holder providing an object or pattern to be viewed by the endoscope, when the endoscope is placed in the holder, and positional elements mounted on the holder at known positions. A processor in the apparatus operates to determine the positions of the tracking and positional elements, with the endoscope shaft received in the holder guide, and calculate from the determined positions, the coordinates of the endoscope lens with respect to the tracking elements, and the field of the view of the lens. Also disclosed is a calibration method which employs the apparatus.

6 Claims, 10 Drawing Sheets

APPARATUS AND METHOD FOR CALIBRATING AND ENDOSCOPE

This application claims the benefit of U.S. Provisional Application No. 60/193,209 filed Mar. 30, 2000, which is incorporated herein by reference in its entirety.

FIELD OF THE INVENTION

The present invention relates to an apparatus method for calibrating lens position and field of view in an endoscope, with respect to a tracking element on the endoscope.

REFERENCES

Asari, K. V., et al., "Technique of distortion correction in endoscopic images using a polynomial expansion," *Med. Biol. Comput.* 37:8–12, (1999).

R. Khadem, C. Yeh, M. Sadeghi-Tehrani, M. R. Bax, J. A. Johnson, J. N. Welch, E. P. Wilkinson, R. Shahidi. "Comparative Tracking Error Analysis of Five Different Optical Tracking Systems". Computer Aided Surgery, Vol. 5, pp 98–107, 2000.

E. Krotkov, K. Henriksen, and R. Kories, "Stereo ranging with verging cameras," *IEEE Transactions on Pattern Analysis and Machine Intelligence*, vol. 12, pp. 1200–1205, 1990.

R. Shahidi, "Applications of virtual reality in stereotactic procedures: volumetric image navigation via a surgical microscope," Ph.D. Dissertation, Rutgers University, Rutgers, N.J., 1995.

R. Y. Tsai, "An efficient and accurate camera calibration technique for 3D machine vision," in Proceedings of IEEE Conference on Computer Vision and Pattern Recognition, 1986, pp. 364–374.

M. Viergever (ed.), "Special Issue on Image-Guidance of Therapy," IEEE Trans on Medical Image, Vol. 17, pp. 669–685 (1998).

D. J. Vining, "Virtual Endoscopy: Is It Reality?" Radiology, Vol. 200, pp. 30–31 (1996).

Weng, J., et al., "Camera Calibration with Distortion Models and Accuracy Evaluation," *IEEE Transactions on Pattern Analysis and Machine Intelligence* 14(10):965–980, (1992).

BACKGROUND OF THE INVENTION

Computer-assisted methods now provide real-time navigation during surgical procedures, including analysis and inspection of three-dimensional (3-D) diagnostic images from magnetic resonance (MR) and computed tomography (CT) data (Viergaver). Endoscopic technology has also undergone rapid development, providing lightweight endoscopes able to be used in small body cavities. Endoscopes are however able to display only visible surfaces, and are also limited by their inability to provide views of the interior of opaque tissue. The combination of both endoscopic and computer-generated 3-D images has the potential to provide the previously unavailable capability of overlaying volumetrically reconstructed patient images onto the endoscopic view of the surgical field. This technique could permit surgeons to look beyond visible surfaces and provide "on-the-fly" 3-D and two-dimensional (2-D) information for planning and navigational purposes (Shahidi, Vining). Due to the many parameters involved in the function of an endoscope, however, multiple small errors in the settings of the device may have relatively large and cumulative effects on the final discrepancy between the position of the overlaid endoscopic images and the patient's anatomy. For this reason, precise calibration of the endoscope and accuracy testing of the calibrated endoscope is necessary to ensure surgical quality. The present invention is directed toward this goal.

SUMMARY OF THE INVENTION

The invention includes, in one aspect, apparatus for use in calibrating lens position and field of view in an endoscope having an elongate shaft and a distal-end lens. The apparatus includes a plurality of tracking elements mounted at fixed positions on the endoscope's shaft, a holder having a guide in which the endoscope can be received to align the endoscope shaft in the holder and position the endoscope lens for viewing a three-dimensional object contained at a target area in the holder, positional elements mounted on the holder at known positions with respect to the guide and three-dimensional object or pattern, and a sensing device for sensing the tracking and positional elements. These elements are used in viewing a known three-dimensional object at known object and endoscope positions in space.

A processor in the apparatus is operably connected to the sensing device and to a display device for carrying out the following operations: (i) determining the positions of the tracking and positional elements, with the endoscope shaft received in the holder guide, (ii) using the determined positions of the tracking and positional elements to place the endoscope and the holder in a common frame of reference, (iii) projecting on the display device, a video image of the three-dimensional holder object as seen by the endoscope with the endoscope shaft received in the holder guide, (iv) projecting a model image of the three dimensional object on the display device, representing the three dimensional object as seen from a known lens position and field of view, and (v) using information about the relative sizes, positions, and orientations of the two images to calculate the coordinates of the endoscope lens with respect to the tracking elements, and the field of the view of the lens.

In a preferred embodiment, using information about the relative sizes, positions, and orientations of the two images includes manually matching the endoscopic and model images, by translating, rotating and/or scaling one or both images, and from the direction and extent of such adjustments, determining the coordinates of the endoscopic lens with respect to the tracking elements, and the field of view of the lens. The information may be further used to correct for lens distortion.

The holder includes a structure, such as a bore, for receiving the endoscope therein or thereon, to place the endoscope at a known axial position with respect to the holder, and preferably includes a stop for arresting the axial position of the endoscope in the holder structure at a known, selected endoscope position.

The apparatus is used in calibrating lens position and field of view in the endoscope, in accordance with another aspect of the invention. The method includes the steps of (a) positioning the endoscope in a holder of the type described above, and (b) employing a sensing device to sense the positions of the endoscope tracking and holder positional elements, with the endoscope shaft received in the holder.

A processor operatively connected to the sensing device and to a display device functions to (i) determine from input provided by the sensing device, the positions of the tracking and positional elements, with the endoscope shaft received in the holder guide, (ii) use the determined positions of the tracking and positional elements to place the endoscope and the holder in a common frame of reference, (iii) project on a display device, a video image of the three-dimensional holder object as seen by the endoscope with the endoscope shaft received in the holder guide, and (iv) project a model image of the three dimensional object on the display device, representing the three dimensional object as seen from a known lens position and field of view, and (v) use information about the relative sizes, positions, and orientations of the two images to calculate the coordinates of the endoscope lens with respect to the tracking elements, and the field of the view of the lens.

Preferably, the two images are aligned by the user, and from the alignment adjustments, the processor calculates the coordinates of the endoscope lens with respect to the tracking elements, and the field of the view of the lens. The display device may include a split screen or two screens for displaying the video and model images separately on first and second screen regions, and the aligning steps may include: (i) rotating one of the images to the rotational position of approximate orientation of the other image, (ii) sizing one of the images to the approximate size of the other image, (iii) superimposing the two images, and (iv) making final adjustments in image orientation and size until the two images overlap.

In another aspect, the calibration apparatus is designed for automated calibration of endoscope lens position, field of view and, optionally, view vector and/or lens distortion. The apparatus includes a plurality of tracking elements mounted at fixed positions on the endoscope's shaft, a pattern support having a feature pattern contained in a target region of the holder, positional elements mounted on the pattern support at known positions with respect to said pattern, and a sensing device for sensing the tracking and positional elements.

A processor in the apparatus functions to (i) determine the positions of the tracking and positional elements, with the endoscope placed at a selected position for viewing features in said pattern in three dimensions, (ii) use the determined positions of the tracking and positional elements to place the endoscope and the holder in a common frame of reference, (iii) determine the image coordinates of features in the pattern, as seen by the endoscope at the selected position, and (iv) use a lens projection algorithm to calculate from the image coordinates of the pattern features, and the known positions of the pattern features in said common reference frame, the coordinates of the endoscopic lens with respect to said tracking elements and the lens' field of view. The processor may be further operable to correct for lens distortion effects, such that the endoscope image displayed on the display device is a true perspective image.

The apparatus may include a user control which, when activated, simultaneously signals the sensing device to sense the tracking and positional elements, and the processor, to record the image seen by the endoscope. This control allows the user to place an endoscope at a selected viewing position with respect to the holder and take a simultaneous snapshot of the endoscope view and endoscope and holder positions, whether or not the endoscope is physically held in the holder.

Where the holder pattern is planar, the endoscope view vector should be at least about 30° off the normal to the pattern plane, to provide view depth information to the processor. Alternatively, the holder may include a curved surface, such as a hemispherical shell, on which the pattern is placed, such that the pattern provides pattern depth information at any selected position at which the endoscope can view the pattern. An exemplary pattern consists of an array of relatively small and relatively large spots, arranged so that each region of the array can be uniquely identified by the pattern of small and large spots therein.

In a related aspect, the invention includes a method for automated calibration of endoscope lens position, field of view and, optionally, view vector and/or lens distortion, employing the above apparatus. The method includes the steps of (a) positioning the endoscope at a selected position with respect to a pattern support, and (b) employing a sensing device to sense the positions of the endoscope tracking and holder positional elements, with the endoscope positioned at the selected position. A processor operatively connected to the sensing device and to a display device operates in the method to: (i) determine the positions of the tracking and positional elements, with the endoscope placed at a selected position for viewing features in said pattern in three dimensions, (ii) use the determined positions of the tracking and positional elements to place the endoscope and the holder in a common frame of reference, (iii) determine the image coordinates of features in the pattern, as seen by the endoscope at the selected position, and (iv) use a camera calibration algorithm to calculate from the image coordinates of the pattern features, and the known positions of the pattern features in the common reference frame, the coordinates of the endoscopic lens with respect to said tracking elements and the lens' field of view.

These and other objects and features of the invention will become more fully apparent when the following detailed description of the invention is read in conjunction with the accompanying drawings.

DETAILED DESCRIPTION OF THE INVENTION

The apparatus and method of the invention will be described with reference to two general embodiments. The first embodiment employs image matching, e.g., by the user, to align an actual endoscopic image with a model image. The endoscope image is of a three-dimensional object provided by an endoscope holder, as seen by the endoscope when the latter is held in the holder at a selected orientation and position. The model image is a displayed image of the three-dimensional object as it would be seen by an endoscope having a known field of view and positioned at a given distance from the object. From the adjustments made by the user to align the two images, and from the known position of the endoscope with respect to the holder object, a processor calibrates the endoscope's lens coordinates and rotational coordinates with respect to tracking elements on the endoscope, and the endoscope's field of view and optionally, lens distortion. This general embodiment is referred to herein as First Calibration Apparatus and Method.

In the second general embodiment, the holder provides a feature pattern that can be viewed in three dimensions, e.g., with depth features, when the endoscope is placed at a selected position with respect to the holder. The endoscope image of the pattern is then matched by a camera calibration algorithm with a model pattern, as seen from a given endoscope position and orientation, to calibrate endoscope lens position and orientation with respect to tracking elements on the endoscope, and endoscope field of view and lens distortion. This embodiment is also referred to herein as Second Calibration Apparatus and Method.

A. First Calibration Apparatus and Method

Figure 1A:
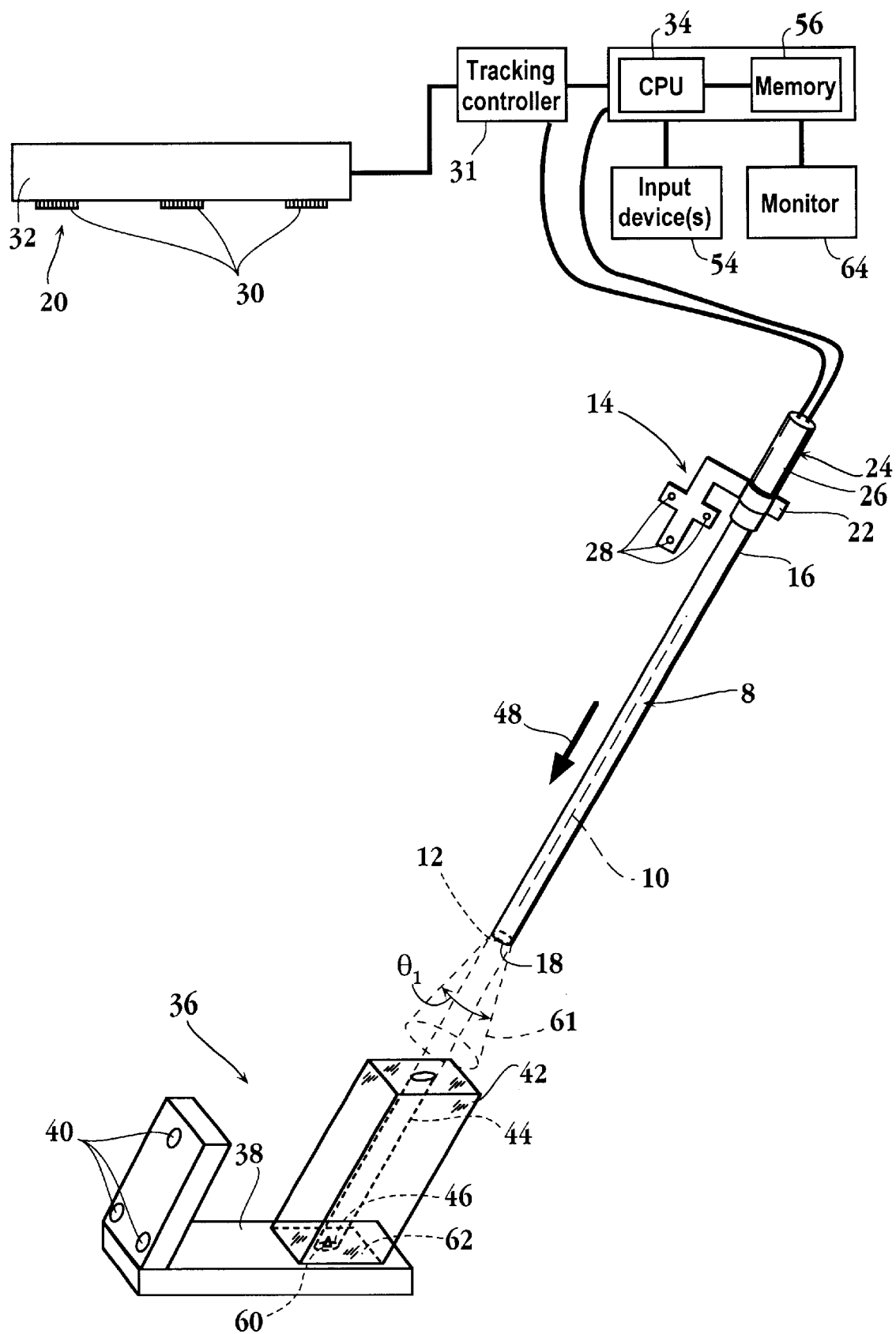
FIGS. 1A and 1B illustrate an endoscope-calibration apparatus constructed according to a first general embodiment of the invention, shown in use with an endoscope before (1A) and after (1B) placement of the endoscope in the holder in the apparatus.
Figure 1B:
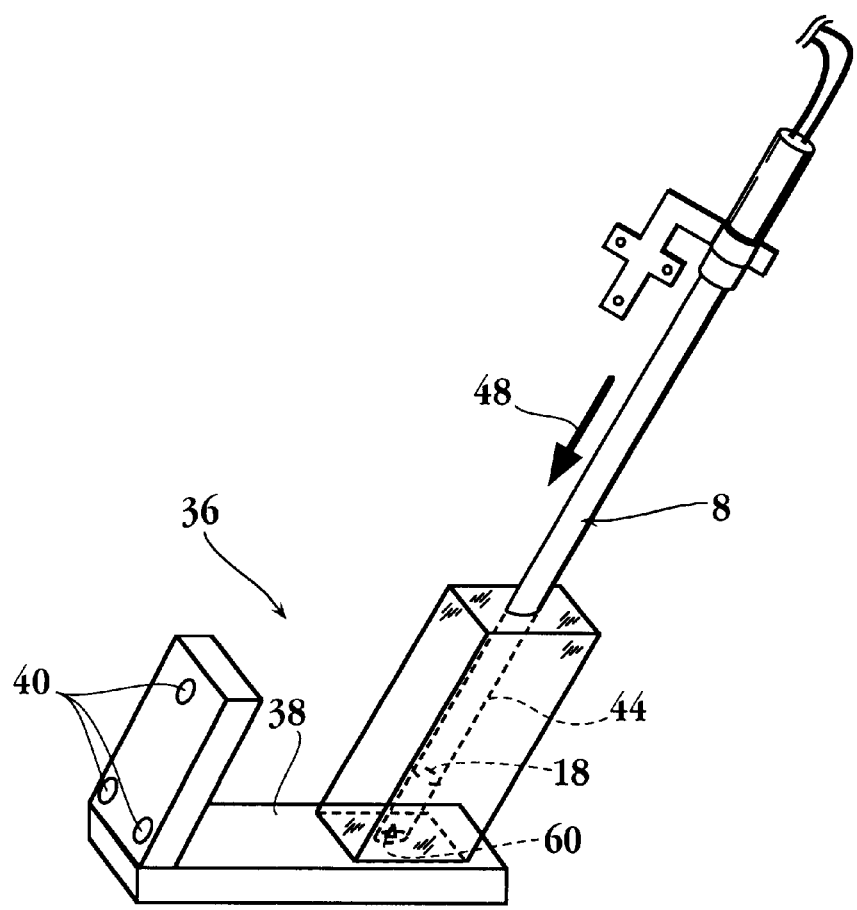

FIGS. 1A and 1B illustrate an endoscope calibration apparatus constructed in accordance with the invention. An exemplary endoscope 8 has an elongate shaft 16 defining a central axis 10, and a distal lens 12 whose view vector, i.e., the direction of view, is aligned with axis 10.

The calibration procedure involves, in part, establishing a geometric relationship between a positional tracking assembly 14 attached to the endoscope, and shaft 16 and the tip 18 of the endoscope. During use of endoscope 8 in surgery, a tracking system 20 tracks the position and orientation of the tracking assembly only. Therefore, the relative position between tracking assembly 14 and the shaft and tip of the endoscope must be determined before use of the endoscope in order to (1) correctly select the position, orientation, and field-of-view (FOV) angle of the 3D volumetric perspective image to be displayed and (2) correctly fuse actual images obtained from the endoscope with 3D volumetric perspective images obtained from the pre-operative 2D scans.

FIGS. 1A and 1B show tracking assembly 14 attached to endoscope 8. The assembly can be attached by use of a detachable device such as a clip 22. As shown in FIGS. 1A and 1B, the assembly is preferably attached to a proximal end 24 of endoscope 8, e.g., to a handle 26 of the endoscope. The assembly provides at least three linear tracking elements 28, such as light emitting diodes (LEDs), located at fixed linear positions on the assembly. The tracking elements are arranged non-colinearly in a plane, as shown in FIGS. 1A and 1B. This arrangement is exemplary only. Other types of tracking assemblies capable of providing information relating to movement of a device having six degrees of freedom are suitable, so as to determine the three-dimensional coordinates of the device as well as the angle of attack $\theta 2$ and the angle of twist $\alpha$ of the attached endoscope (as described below).

In the illustrated embodiment, tracking elements 28 (e.g., LEDs) emit continuous streams of pulsed infrared signals which are sensed by a plurality of infrared detectors 30 mounted in a sensing device 32 in view of endoscope 8. The endoscope and the sensing device are both in communication with a tracking controller 31 which controls the timing and synchronization of the pulse emissions by the LEDs and the recording and processing of the infrared signals received by the detectors 30. The tracking controller is in communication with a CPU 34 which processes the digital signals received from the tracking controller. Tracking device 14, sensing device 32 and tracking controller 31 form part of an optical tracking system (OTS). The OTS may be controlled by software which resides in memory 56 and is executed by the CPU for processing the incoming signals from the tracking controller to generate data and images indicating the location and orientation of the endoscope. The OTS can generate location and orientation data on a continuous, real-time basis, so that during calibration, as described herein, or as endoscope 8 is moved during surgery, its position and orientation are continually tracked by sensing device 32 and recorded in memory 56. The OTS may be of the type known as the "FlashPoint 3-D Optical Localizer," which is commercially available from Image Guided Technologies of Boulder, Colo., similar to the systems described in U.S. Pat. Nos. 5,617,857 and 5,622,170. However, as previously noted, the invention is not limited to any particular OTS; other position tracking systems, such as sonic position detecting systems, magnetic tracking systems, or radio transmitters, may also be utilized.

In FIGS. 1A and 1B there is also shown a holder 36 including a base plate 38. The holder includes positional elements 40, which may be in the form of LEDs, mounted at known positions with respect to a guide 42. In the embodiment shown, the guide has a channel 44 therethrough for slidably receiving the endoscope, as shown in FIG. 1A. When endoscope 8 is held within guide 42, as in FIG. 1B, a selected reference point on the endoscope is placed at a known position within guide 42. For example, when the position of a lower end 46 of the guide in relation to positional elements 40 is predetermined, and endoscope 8 is inserted into the guide, the location of its tip 18 becomes a known reference point. This position can be established, for example, by including a stop in the holder which arrests axial movement of the endoscope at a selected position, or by placing a ring or other stop member on the endoscope, to likewise arrest axial movement of the endoscope within the holder guide.

It is therefore important for the calibration and compensation procedures that the instrument fit snugly in the guide so that the tip or other reference point on the instrument is fixed relative to positional elements 40. Preferably, the instrument tip is centered within the guide. Thus, the channel may be of a dedicated-diameter in order to accommodate a specific instrument or type of instrument. Alternatively, the channel holder may have a variable diameter that may be adjusted manually (e.g., with a screw, chuck or equivalent device) or automatically (e.g., with a motor-gear assembly).

In one of the illustrated embodiments, the channel may be of a fixed diameter large enough to accommodate many different types of medical instruments which require calibration. In this case, a smaller-diameter instrument may be calibrated using a larger-diameter channel holder by employing a sheath or the like over the endoscope shaft. Such a sheath would have an outer diameter just less than the diameter of the holder channel and an inner diameter just greater than the diameter of the endoscope shaft.

Figure 1C:
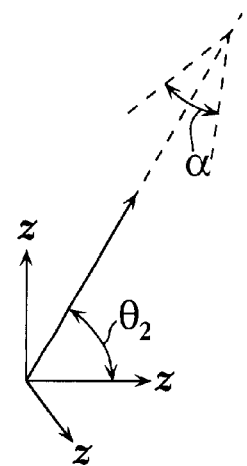
FIG. 1C illustrates the endoscope-sheath assembly angle within the guide.

Before calibration, the endoscope-sheath assembly is inserted into guide 42 in the direction of arrow 48 and is snugly retained within the guide at an angle $\theta_2$ which has been predefined in relation to positional elements 40. The angle of attack $\theta_2$ is shown in FIG. 1C, in which endoscope 8 is represented by an arrow 50 within a coordinate system.

The calibration procedure is initiated by user command which can be implemented by any convenient input device 54 such as a foot pedal, voice command, mouse, stylus, or keyboard.

During calibration, the endoscope remains seated within guide 42, during which time the LEDs 28 and 40 are tracked by detectors 30 mounted overhead on sensing device 32 in view of both positional elements 40 and tracking device 14 on the endoscope. These signals are then relayed to the tracking controller, which is in communication with sensing device 32 as shown in FIGS. 1 and 2, where the relative positions and orientations of tracking device 14 and positional elements 40 are determined. More specifically, the tracking controller or the CPU determines the relative positions and orientations of the tracking and positional elements 28 and 40 respectively, and determines from these relative positions, the positions of tracking elements 28 with respect to the reference point on endoscope 8. For example, the tracking system or CPU determines the position and orientation of tracking device 14 in relation to the position of tip 18 and the orientation of shaft 16 of the endoscope. These relationships are stored in memory 56 for later use during surgery. The geometric data relating the tracking device and the endoscope is stored in computer memory 56 and remains invariant throughout the subsequent surgical procedure. If the same tracking device 14 is removed and placed on another medical instrument, then another calibration procedure is performed.

Calibrating the medical instrument, as described above, not only enables more accurate tracking of the instrument during a subsequent surgical procedure, but also improves a process of establishing the FOV angle $\theta_1$ of the endoscope lens 12 to enable accurate fusing during the surgical procedure of the endoscopic image with 3D perspective volumetric images constructed from preoperative or intraoperative scan data. In fusing these two types of images, it is important to use the same FOV angle by both the endoscope and the computer generated images so that the images can be registered together.

To this end, holder 36 includes a three-dimensional calibration pattern or object 60—here a regular pyramid—supported on a stage 62 in the holder, for viewing by endoscope lens 12 when the endoscope is placed in holder 38. That is, the object or pattern is positioned in a cavity formed at the base of the channel and is preferably centered so that it is aligned with central axis 10 of the inserted endoscope when it is inserted in channel 44 and aimed at the pattern whose position and orientation is precisely known in relation to positional elements 40. In one preferred embodiment, the object is a three-dimensional geometric object, such as a regular pyramid. In another, the object is a grid of raised objects. In either case, the endoscopic image of the object has three-dimensional of depth features.

Figure 2A:
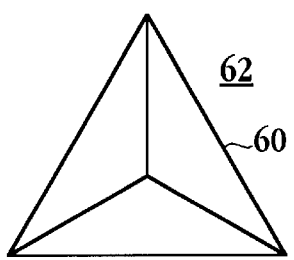
FIGS. 2A and 2B illustrate a solid object provided by the apparatus holder and as seen by endoscope when positioned in the holder.
Figure 2B:
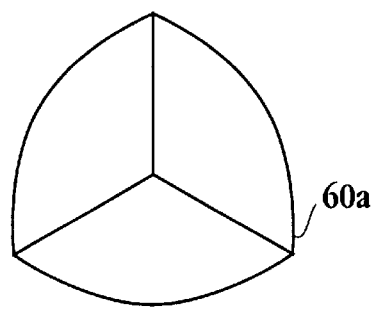

FIG. 2A is a top view of a regular pyramid 60 supported on the stage 62, as the object would be seen by the endoscope, when placed at a selected position within holder. The image as seen by the lens, called the "video image" or "endoscope image" is shown at 60a in FIG. 2B. In carrying out the invention, and with reference to FIGS. 3A–3E, this video image is displayed on one screen A of a two-screen display device, that is either a single split screen with split regions A and B, or two separate display screens A and B. A model image 65a of the same object is displayed on a second screen or screen portion B, and is a screen image of the same object as viewed through a lens with a known field of view, and at a known lens position with respect to the object, and known view vector (typically aligned the endoscope shaft). In the method illustrated and described below, the user will manipulate one of both images to bring them into alignment. These manipulation will involve (i) translating one or both images, i.e., moving the images in a side-to-side (x) or up/down (y) direction; (ii) rotating one or both images about a fixed axis; and (iii) scaling one or both images, e.g., to expand or contract the images in either or both of the x and y directions. The extent of adjustments made to both images to bring them into alignment is then used to determine appropriate transforms for position, rotation, and field-of-view transforms between the model image and video image, thus to determine the lens position and endoscope rotational position with respect to the tracking elements and the endoscope lens field of view, as will be described with reference to FIGS. 4 and 5.

Figure 3A:
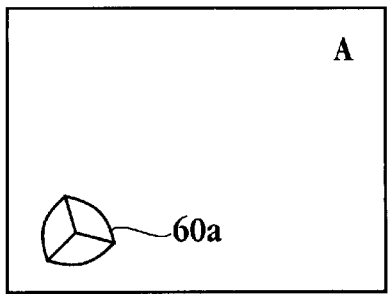
FIGS. 3A–3E illustrate various exemplary images during a matching of model and video images, in accordance with the method of the invention.
Figure 3B:
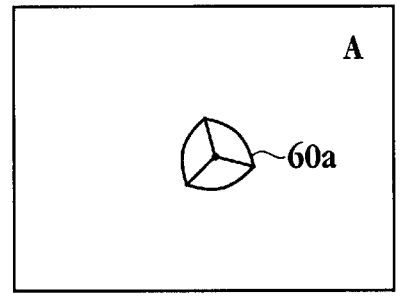
Figure 3C:
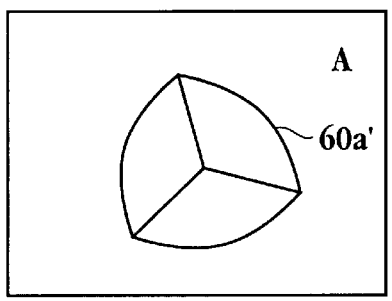
Figure 3D:
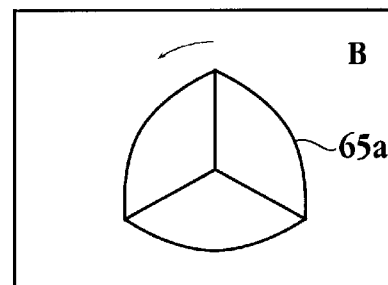
Figure 3E:
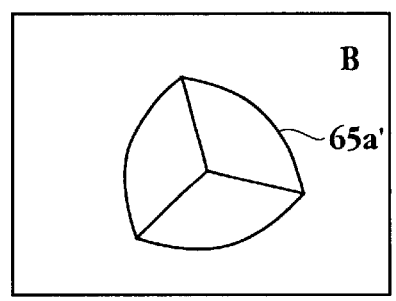

FIGS. 3A–3E illustrate the types of image adjustments employed by the user to align a video image 60a with a model image 65a. Initially, the video image, such as shown in FIG. 3A, is moved by x,y adjustments toward the center of the screen, as in FIG. 3B. The image is then expanded to fill a large portion of the screen, indicated by the expanded image 60a' in FIG. 3C. Screen B in FIG. 3D shows a model image 65a at the center of the screen, and at a given rotational position. The user rotates this image to a position like that of image 60a' in FIG. 3C, then expands the image to approximate the size of image 60a, giving the rotated expanded image 65a' seen in FIG. 3E. The two images, which are now roughly matched in x,y position, rotational position, and scale, are superimposed, allowing the user to make final position and scaling adjustments to bring the two images into alignment, as indicated in the figure.

Figure 4:
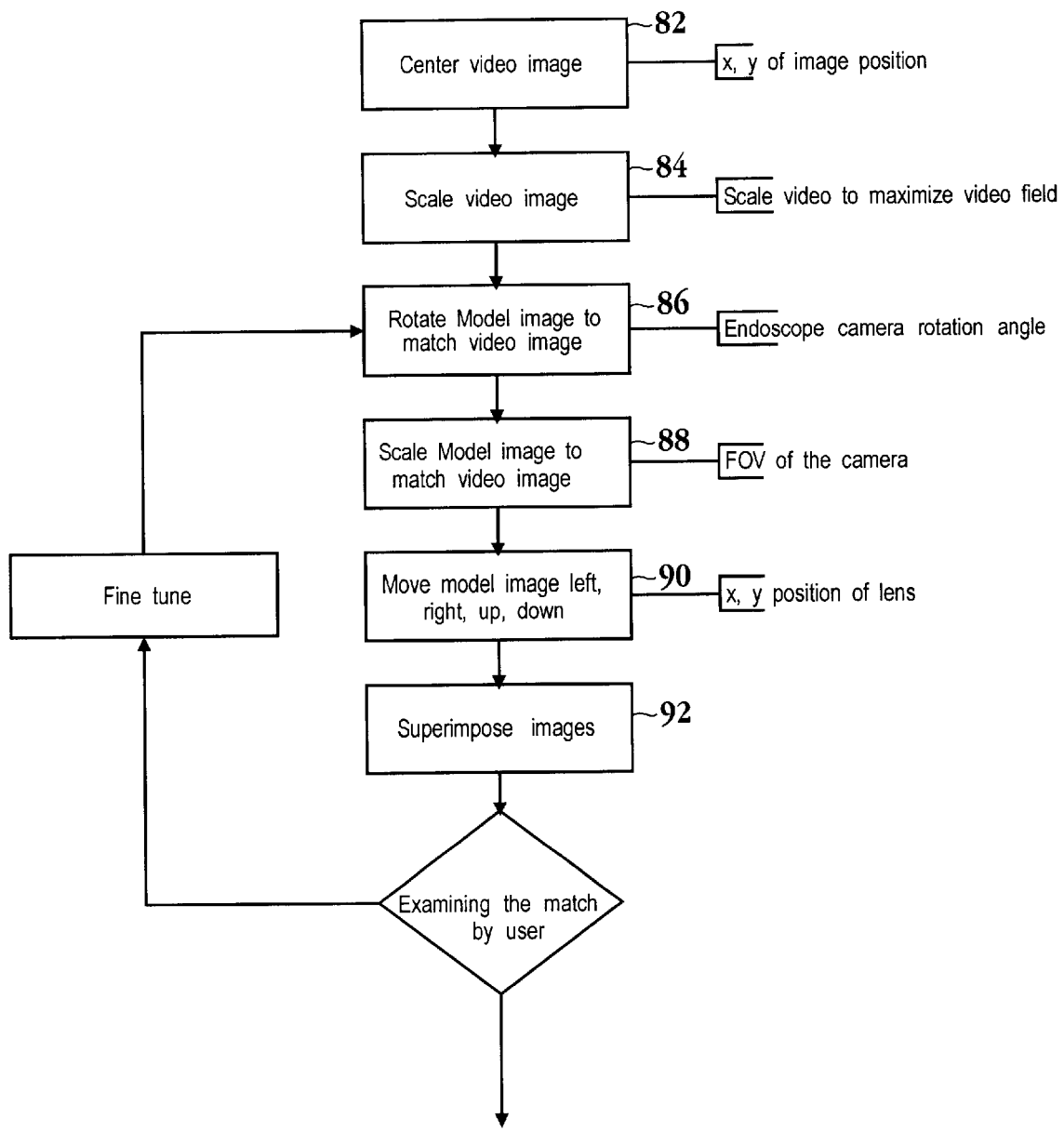
FIG. 4 is a flowchart of the image matching steps of FIGS. 3A–3E.

The image matching operations just described are shown in flow diagram form in FIG. 4. Initially, the video image centered, as at 82, by controlling x,y adjustments in screen (FIGS. 3A and 3B), then scaled to maximize the video field, as at 84, and illustrated in FIG. 3C. One of the two images, in this case, the model image, is then rotated to match the other, as at 86, scaled as at 88 to give the two images roughly the size, and translated, as at 90, to place the two images in the center of the screen. The two images, which now have roughly the same screen position, size and orientation, are now superimposed, as at 92, allowing further fine adjustment until the two images are precisely aligned.

Figure 5:
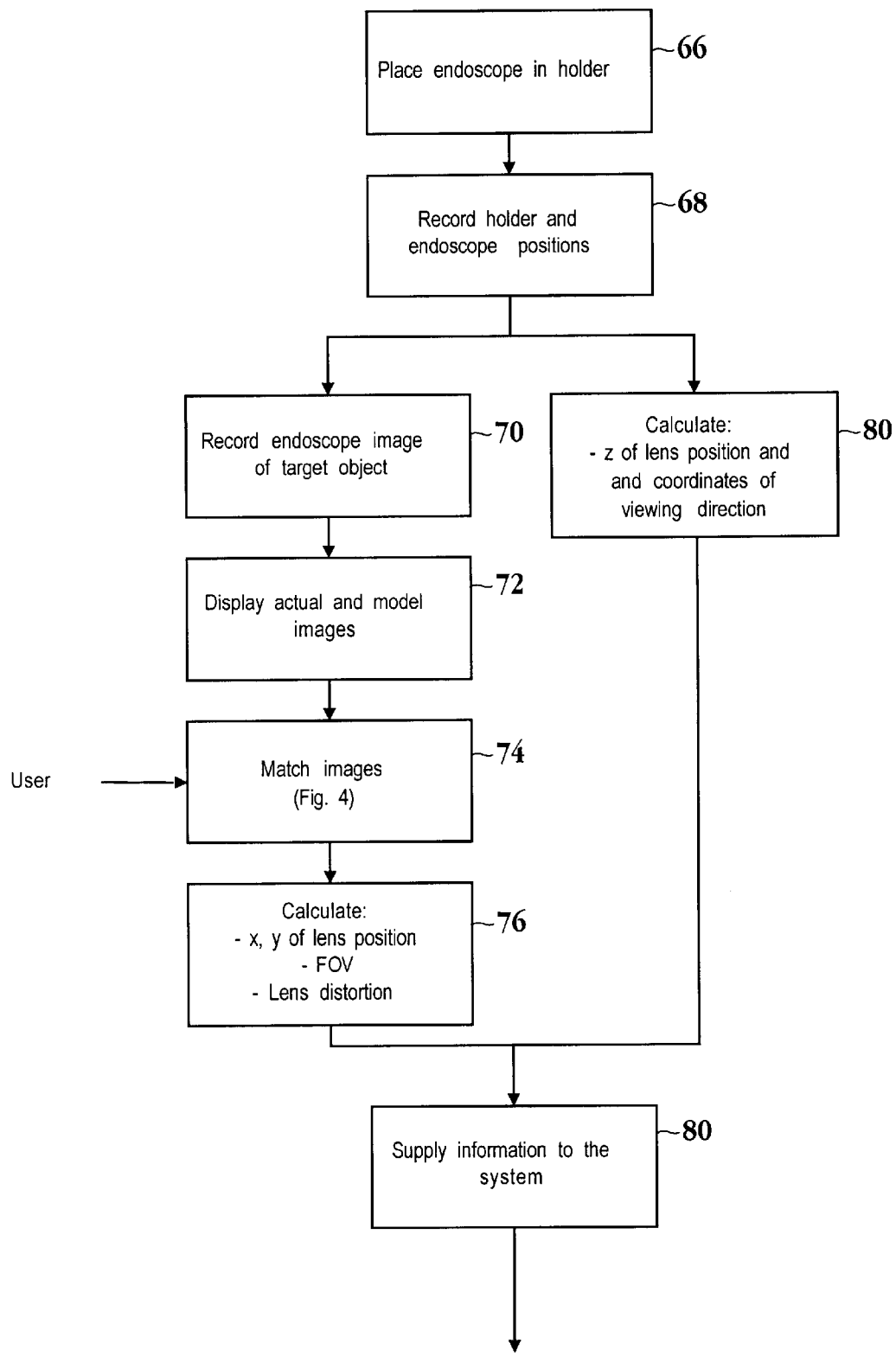
FIG. 5 is a flowchart of the calibration operations carried out by the apparatus, in the first embodiment.

FIG. 5 illustrates steps in carrying out the calibration method, employing the apparatus of the invention. Preferably, calibration, including determination of the FOV angle, are performed at the same time along with any other such pre-surgical instrument adjustment procedures, while the endoscope is retain in holder 36.

After the pattern and endoscope are appropriately positioned, as indicated at 66 in FIG. 5, the positions of the tracking elements on the endoscope and the position elements on the holder are recorded by the sensing device and stored in the CPU (or processor), as at 68. At the same time, the endoscope captures an image of the pattern which is transmitted to the CPU through an appropriate video cable schematically shown in FIG. 1A. This video image is processed and displayed on a display screen 62 side-by-side with a computer-generated model of the same object or pattern, as described above, and indicated at 72 in FIG. 5. As noted above, the model image simulates a camera image in which optical properties, such as focal length, FOV angle, and distance to the pattern or object can be varied. The data for the computer-generated perspective model is retrieved from computer memory 56. An example of a suitable display device is a CRT monitor 64, as shown in FIG. 1A.

The two images are adjusted, as at 74, following the method described above and illustrated with respect to FIGS. 3 and 4. From these adjustments, the x,y position of the lens, the field of view, and optionally, lens distortion are calculated, as at 76, for use by an image reconstruction system, as at 78, for reconstructing images as would be seen by an endoscope having the calculated x,y coordinates and FOV angle.

The positions of the tracking and position elements recorded by the sensing device are used to determine the z position of the endoscope lens (the position along the endoscope axis), as at 80. From the amount of rotation needed to bring the video image into alignment with the model image, the rotational position of the endoscope of with respect to the tracking elements is also determined. The view vector, if it is not aligned with the endoscope shaft can also be determined with respect to the tracking elements.

With the above combined calibration, the system now know the endoscope lens coordinates, rotational position, and view vector with respect to the endoscope tracking elements, and the field of view of the endoscope lens. Thus, with the endoscope placed at any given position in space, and knowing the coordinates of the tracking elements, the system can reconstruct a virtual image, e.g., a subsurface image, as this would be seen by the endoscope, based on the known, calibrated lens coordinates, rotational position, view vector, and field of view of the endoscope.

The image matching can be performed manually or can include automated procedures, as described with respect to the Second Apparatus and Method below. As discussed above, manual matching of the images involves changing the FOV angle of the simulated camera, such that the video appears the same size as the model image. Automatic matching involves a calculation or counting by the CPU of the number of grids visible in image and a determination of the FOV angle based on the number of grids and the distance between the pattern and the endoscope. After the matching, the FOV angle of the 3D perspective image is determined and is stored in memory 56, and is applied to all appropriate subsequently displayed 3D perspective images.

In another aspect of the invention, the CPU is further operable, by user matching of the size and orientation of the two images, to correct for endoscope lens distortion effects, such that endoscope image displayed is a true perspective image. It is known, for example, that the images produced by all real lenses are spherically distorted due to the curved surface of the lens.

For example, the image 60 obtained by endoscopic lens 12 may appear distorted in ways such as fish eye distortion or pincushion distortion. To compensate for this distortion effect, in accordance with the invention, 3D perspective image can be modified morphed so that it matches distorted image 60 obtained by the endoscope 8.

In the described embodiment, 3D perspective image is adjusted to match the video image produced by the endoscope. However, in an alternative embodiment, image 6 produced by the endoscope can itself be adjusted by image processing means known to those skilled in the art. The image obtained by the endoscope can be adjusted to minimize or eliminate spherical distortion, e.g., to appear as seen in a Gaussian coordinate system (planar image), prior to matching with the 3D perspective image.

The lens distortion correction may be performed by determining and recording the coordinates of each of the grid points in image 60, and by iteratively minimizing a cost function for the updated distortion model. The cost function may be the root-mean-squared (RMS) value of the error between the recorded coordinates and predicted coordinates for the current distortion model. A distortion model may include radial distortion, astigmatism distortion, angular distortion, etc.

The compensations made during the calibration procedures described herein are retained within memory 56 and applied to all appropriate subsequently displayed 3D perspective images or endoscopic images.

As previously noted, various aspects of the invention may be implemented by a program of instructions (e.g., software) executed by CPU 34. One such aspect includes processing user input data and the data to determine the relative positions and orientations of the tracking and positional elements 28 and 40 respectively, and to determine from these relative positions, the positions of the tracking elements 28 with respect to the reference point (i.e., the tip 18) on the endoscope. Another aspect of the invention which may be software-implemented is the processing of data to generate and render images in connection with the determination of the FOV angle $\theta_1$ and the distortion and offset compensation procedures.

The software for such task(s) may be fetched for execution by the CPU from memory 56 which is in communication with the CPU and which may include random-access memory (RAM) and/or read-only memory (ROM). The software may be conveyed to the memory, or alternatively may be transmitted directly to the CPU for execution, through an appropriate disk drive, modem or the like in communication with CPU 34. More broadly, the software may be conveyed by any medium that is readable by the CPU. Such media may include, for example, various magnetic media such as disks or tapes, various optical media such as compact disks, as well as various communication paths throughout the electromagnetic spectrum including signals transmitted through a network or the internet including a carrier wave encoded to transmit the software.

As an alternative to software implementation, the above-described aspects of the invention may be implemented with functionally equivalent hardware using discrete components, application specific integrated circuits (ASICs), digital signal processing circuits, or the like. Such hardware may be physically integrated with the CPU or may be a separate element which may be embodied on a computer card that can be inserted into an available card slot in the computer.

Thus, the above-described aspects of the invention can be implemented using software, hardware, or combination thereof. The description and drawings provide the functional information one skilled in the art would require to implement a system to perform the processing required.

B. Second Calibration Apparatus and Method

Figure 6:
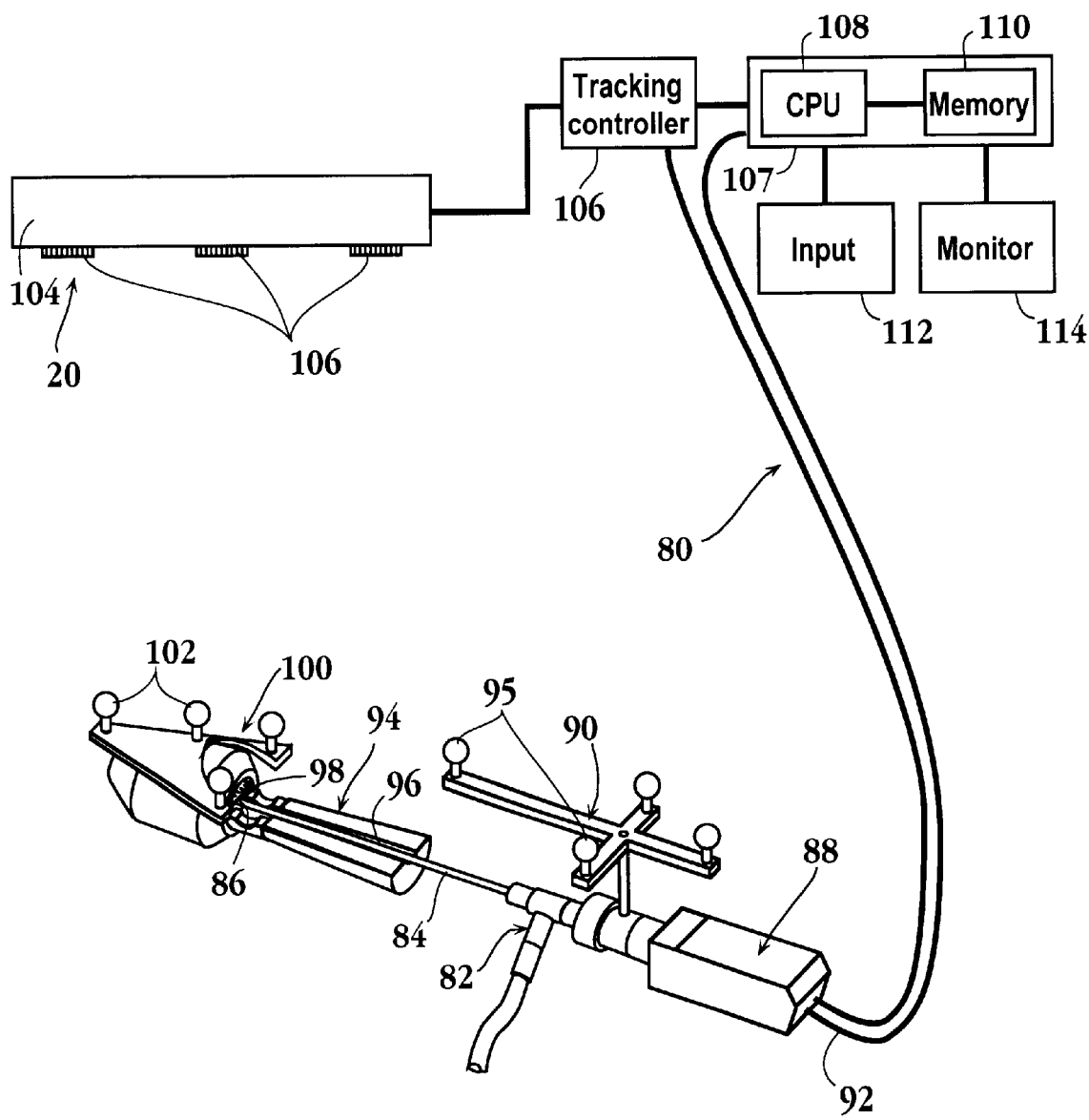
FIG. 6 illustrates an endoscope-calibration apparatus constructed according to another general embodiment of the invention, shown with an endoscope shaft cradled in a holder in the apparatus.

FIG. 6 shows an endoscope calibration apparatus constructed according to another general embodiment of the invention, for calibrating the lens position, orientation, field of view and optionally, lens distortion, of an endoscope 82. As above, endoscope 82 includes an elongate shaft 84 terminating at a distal-end lens 86 which may be mounted for viewing along the endoscope shaft axis, or may have an angled view vector, e.g., angled 30° with respect to the shaft axis. According to an important feature of this embodiment of the invention, and as will be seen below, the endoscope can be calibrated without being physically connected to the holder when the view vector is aligned with the shaft axis.

A handle 88 in the endoscope is used to guide the scope, conventionally, and includes a control button (not shown)

that the user activates to initiate a calibration operation, when the endoscope is placed on the apparatus or held by the user at a selected position with respect to the apparatus. This button connects to control elements of the apparatus as shown. Finally, the endoscope includes a tracking assembly 90 having four tracking elements, such as elements 95, for tracking the position of the endoscope in the coordinate system of the surgical environment, as described above. As above, at least three-non-linear tracking elements are required.

Apparatus 80 includes, in addition to the just-mentioned endoscope tracking assembly, a holder 94 which provides a cradle 96 in which the shaft of the endoscope can be placed, for holding the shaft at a known orientation with respect to the holder, and a feature pattern 98 which is the calibration pattern used in the method, similar to the three-dimensional object employed in the first embodiment. Various planar and curved-surface patterns will be described below with respect to FIGS. 7 and 8. At this point, it is noted only that the pattern preferably has an array of features, such as a pattern of dots or different sizes, that allows any region of the pattern to be uniquely identified by the pattern in that region, and (ii) the pattern is viewed by the endoscope lens so as to provide pattern depth information. As will be seen below, this may be accomplished by viewing a planar pattern (FIGS. 7A and 7B) at an angle, or by viewing a pattern formed on a curved surface, such as a hemispherical shell (FIGS. 8A and 8B).

Holder 94 is also provided with a tracking assembly 100 having four positional elements, such as elements 102, for tracking the position of the holder in the coordinate system of the surgical environment, also as described above. The positions of the holder and endoscope are tracked, during an endoscope-calibration operation, by sensing device 104 which is secured at a fixed position suitable for receiving signals form or emitting signals to the two tracking assemblies, as described for the first embodiment of the invention. The sensing device is operably connected to a tacking controller 106 which in turn is operably connected to a processor 106 having a CPU 108 and memory 108, and connected to a display device or monitor 114, and receiving selected user inputs from input devices 112. The operational features of the processor, in carrying out the calibration method of the invention, will be apparent from the method operation described below.

Figure 7A:
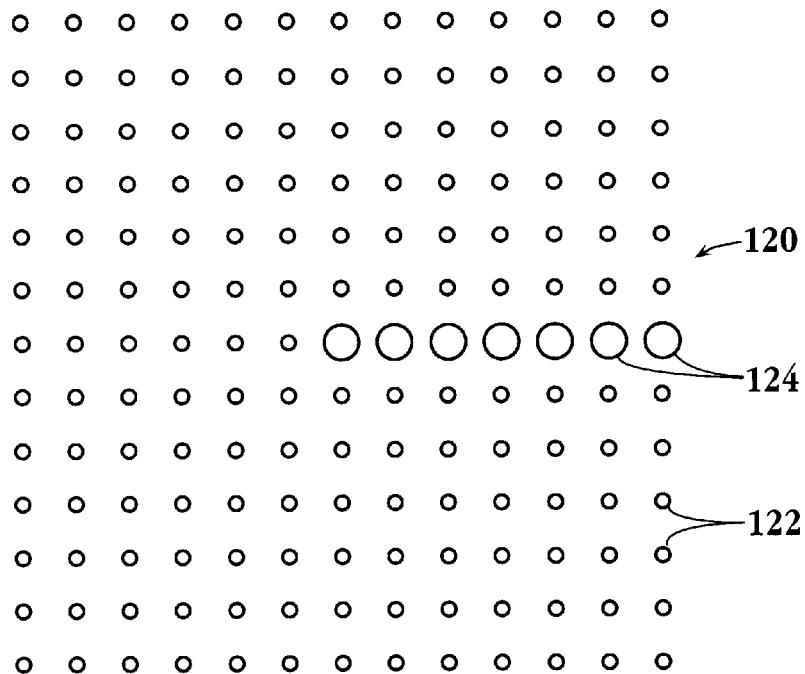
FIGS. 7A and 7B illustrate a planar dot pattern provided by the apparatus holder (7A) and as seen by the endoscope (7B) when positioned in the holder to view the pattern at an angle of greater than about 30°.
Figure 8A:
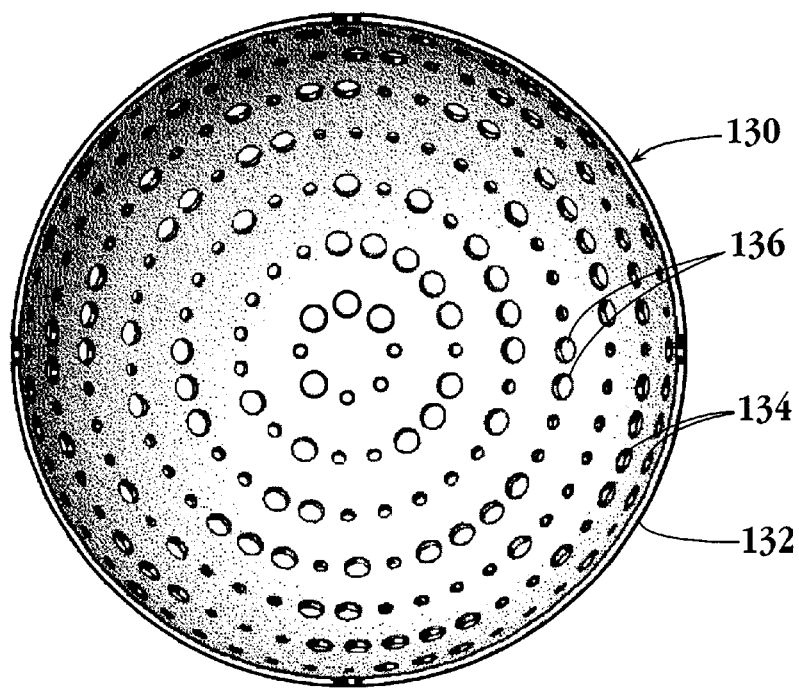
FIGS. 8A and 8B illustrate a hemispherical dot pattern (8A) provided by the apparatus holder, in another embodiment, as seen by endoscope when positioned in the holder (8B)
Figure 8B:
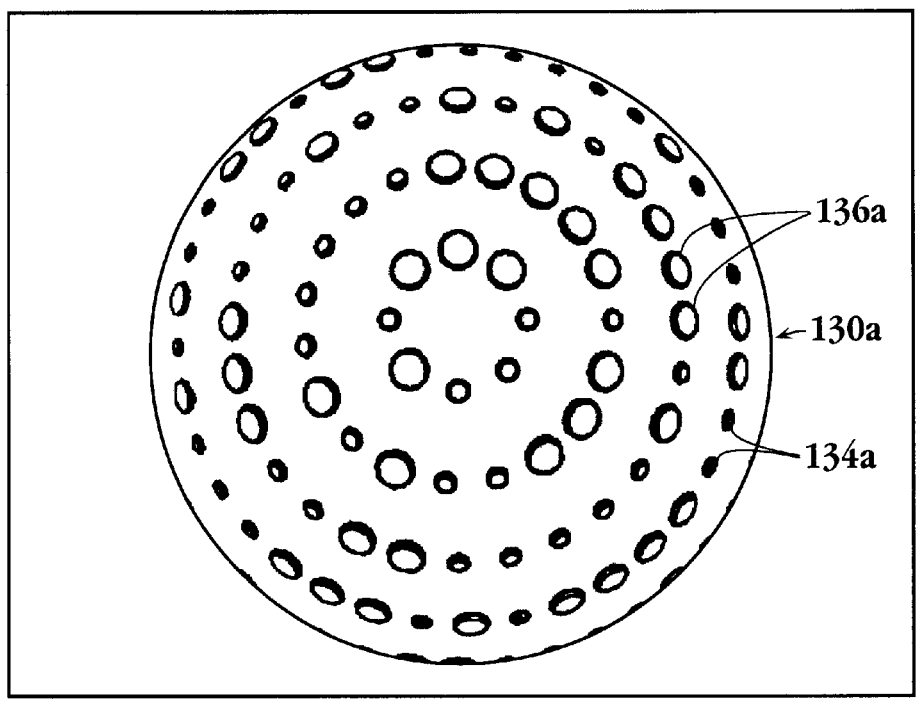

FIG. 7A shows a planar feature pattern 120 suitable for use in the invention, and supported on a planar surface in a holder of the type described above. In particular, the pattern is carried on a planar surface at an angle preferably at least about 30° from the axis of the endoscope's view vector, when the endoscope shaft is placed in the holder cradle. Thus, for example, when the view vector is aligned with the endoscope handle, the axis of the handle makes an angle of at least about 30° with a line normal to the pattern surface. The pattern is composed of an array of relatively small dots or spots 122, and relatively large dots 124, it being recognized that the two classes of dots may be characterized by different sizes (as shown), different colors, or different shapes.

Figure 7B:
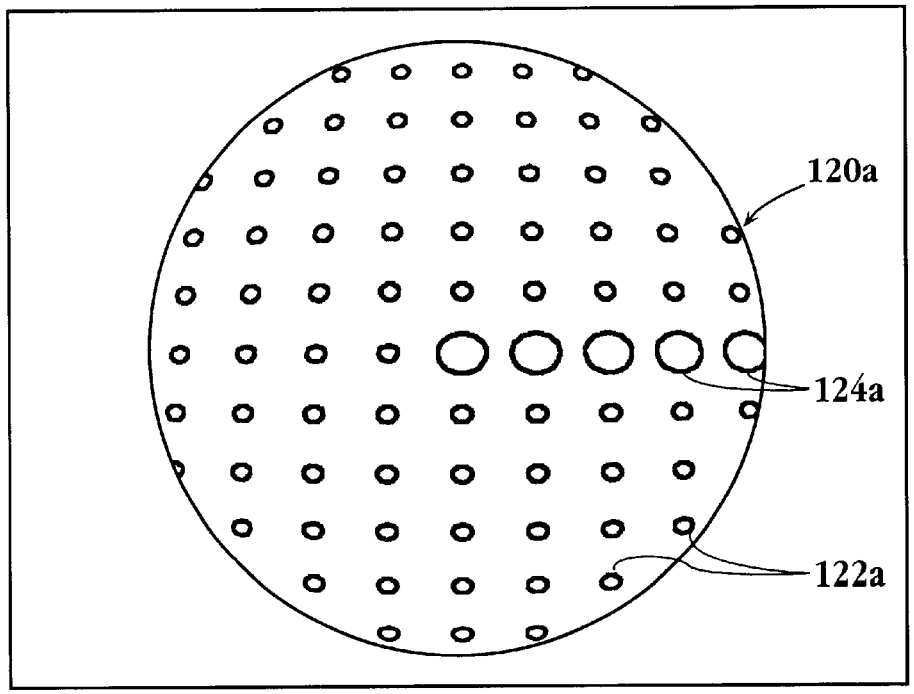

FIG. 7B shows the same pattern 120a of large and small dots 124a, 122a, respectively, as seen through an endoscope lens, e.g., when an endoscope is cradled in the holder and the view vector is aligned with the endoscope shaft. As can be appreciated, the pattern of small and large dots allows each the particular region being viewed, and each pattern spot being viewed, to be identified with a particular dot in the planar pattern. In addition, the spacing between adjacent dots provides both pattern-depth and lens distortion information, as will be seen.

FIG. 8A shows a feature pattern 130 formed on the interior of a hemispherical shell 132 in a holder. The pattern consists of large and small dots, such as dots 134, 136, having a unique arrangement of the two different sized dots in each region of the pattern. The same pattern as seen through an endoscope lens in shown at 130a in FIG. 8B. As can be appreciated, based on the arrangement of different sized dots, such as large dots 136a and smaller spots and in the image, the correspondence between each dot in the pattern and dot spot in the image can be readily determined, and thus the distance relationships between and among dots in the image, as seen through the endoscope lens, and also as affected by lens distortion, can be readily quantitated.

Figure 9:
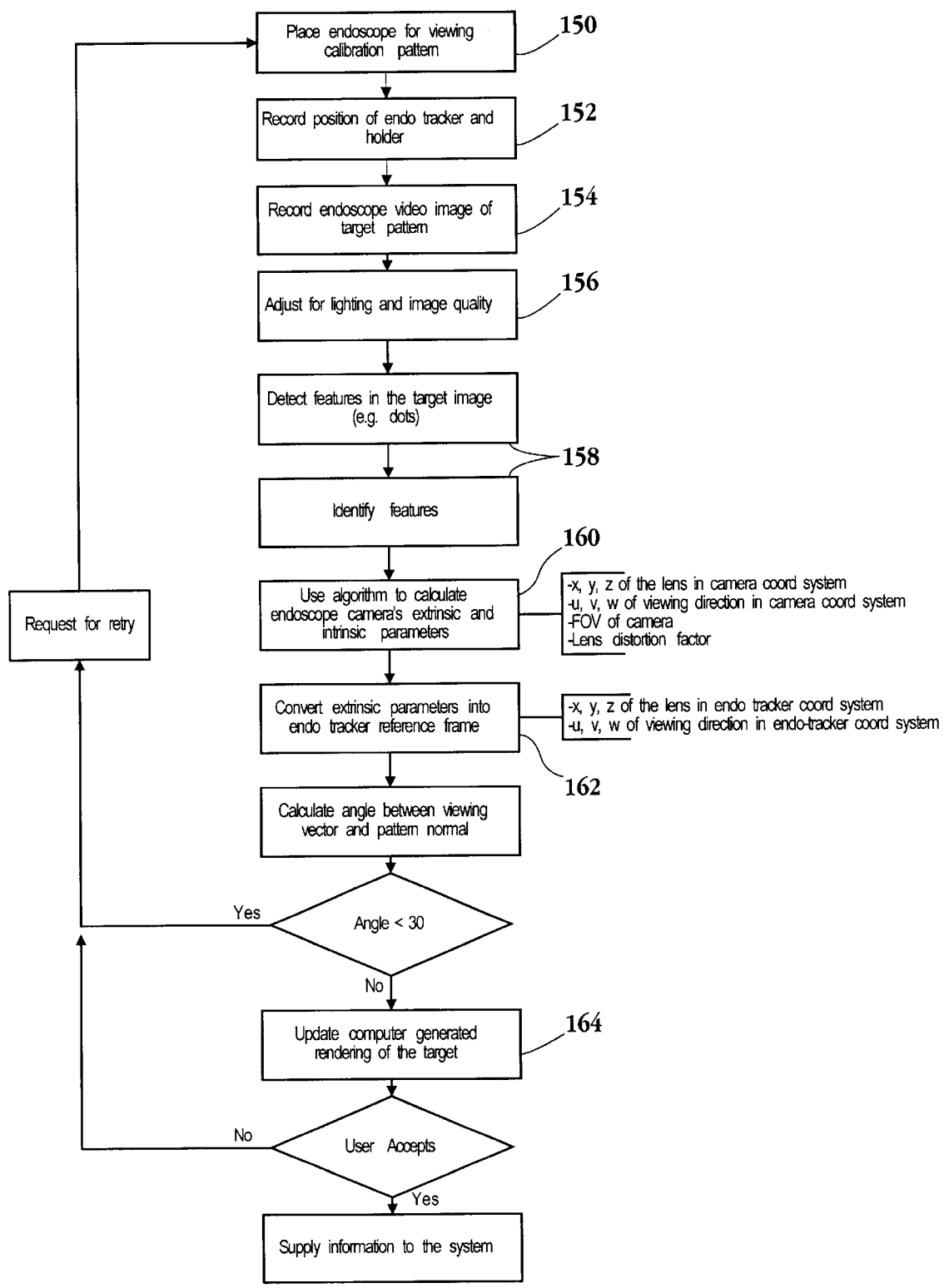
FIG. 9 is a flowchart of the calibration operations carried out by the apparatus, in the second embodiment.

FIG. 9 is a flow diagram of the steps in the method of the invention, as carried out by the user and processor in the apparatus. Initially, the user places the endoscope at a selected position with respect to the holder, as at 150, for endoscope viewing of the feature pattern in the holder. As indicated above, where the view vector is aligned with the endoscope shaft, it is not necessary to place the endoscope shaft in the cradle of the holder, only to place the endoscope for viewing the holder pattern at a position which provides depth information. If the holder provides a planar pattern, the endoscope should be positioned at an angle of at least 30° with respect to a line normal to the pattern plane; for a pattern formed on a curved surface, a variety of view angles may be selected. For an endoscope having a view vector that is not coincident with the endoscope, the endoscope shaft should be placed in the holder cradle, to provide a known endoscope shaft orientation.

Next, the user signals the apparatus to record the positions of the endoscope tracker elements and holder positional elements, as at 152, and at the same time, record the endoscope image at the recorded position, as at 154. The video image produced, such as indicated in FIGS. 7A and 8B, may be automatically enhanced by the processor, as at 156, and the processor than records the size (feature detection) and x,y coordinates of each of the dots in the image, as at 158. The signaling may also be designed to occur when the endoscope and holder are held at fixed calibration position for some given period of time.

The video image is processed, by a processor camera-calibration algorithm indicated at 160, to determine (i) the x,y,z coordinates of the endoscope lens and the orientation of the endoscope view vector with respect to the endoscope tracking elements, and (ii) the field of view and optionally, lens distortion in the endoscope lens. The algorithm used is a so-called camera-calibration algorithm, such as the one reported by Tsai (Tsai). The input parameters to the algorithm are the world coordinates (x, y, z) of a set of known points and their corresponding u, v coordinates in the endoscope video image. The features are identified in the camera image and mapped to the reference pattern; in this way, the real-world coordinates of the features can be found. The best results are obtained when the collection of points are distributed across x, y, and z in world coordinates, and fill as much of the camera image as possible.

For example, in an apparatus having the planar dot pattern of FIGS. 7A and 7B, the world coordinates of the dots are defined with respect to a tracking tool rigidly attached to the calibration unit. The endoscope, equipped with the universal tracker, is then placed into the holder with its lens a selected distance, e.g., 15 mm, from the center of the pattern. In order to achieve a sufficient distribution of the points in the z-direction, the telescope lens view direction is constrained to an angle of 30° from the normal of the pattern plane.

As seen in FIG. 9, the algorithm first calculates a number of camera parameters in the camera coordinate system, as at 160. Using position information from the tracking feature of the apparatus, the lens coordinates and viewing direction are then placed in the coordinate system of the tracking system, as at 162. As an additional feature, the angle of the viewing vector with the pattern normal is calculated, and if less than 30°, (for a planar pattern) the user the user may have the choice of a second recording to achieve a more accurate and reliable calibration. The calibration information from the system is then supplied to the image system for use in an image-guided endoscopic procedure that allows 3-D image reconstruction from the position and FOV of the endoscope.

One of the parameters determined by this algorithm is the lens distortion parameter $\kappa_1$, a coefficient of the cubic radial lens distortion model. Incorporating this nonlinear model into the 3D perspective rendering engine results in a drop in performance; if this lens distortion compensation is omitted, a choice has to be made about the effective FOV of the virtual endoscope. If this FOV is set to match that of the physical endoscope, the result is that the center part of the virtual image is smaller than that in the video image. This effect is undesirable because this is the primary region of interest for the surgeon. An alternative method, here named "constant-radius linear compensation" is to scale the virtual FOV such that the radii of the region of interest in each image are made equal.

Figure 10:
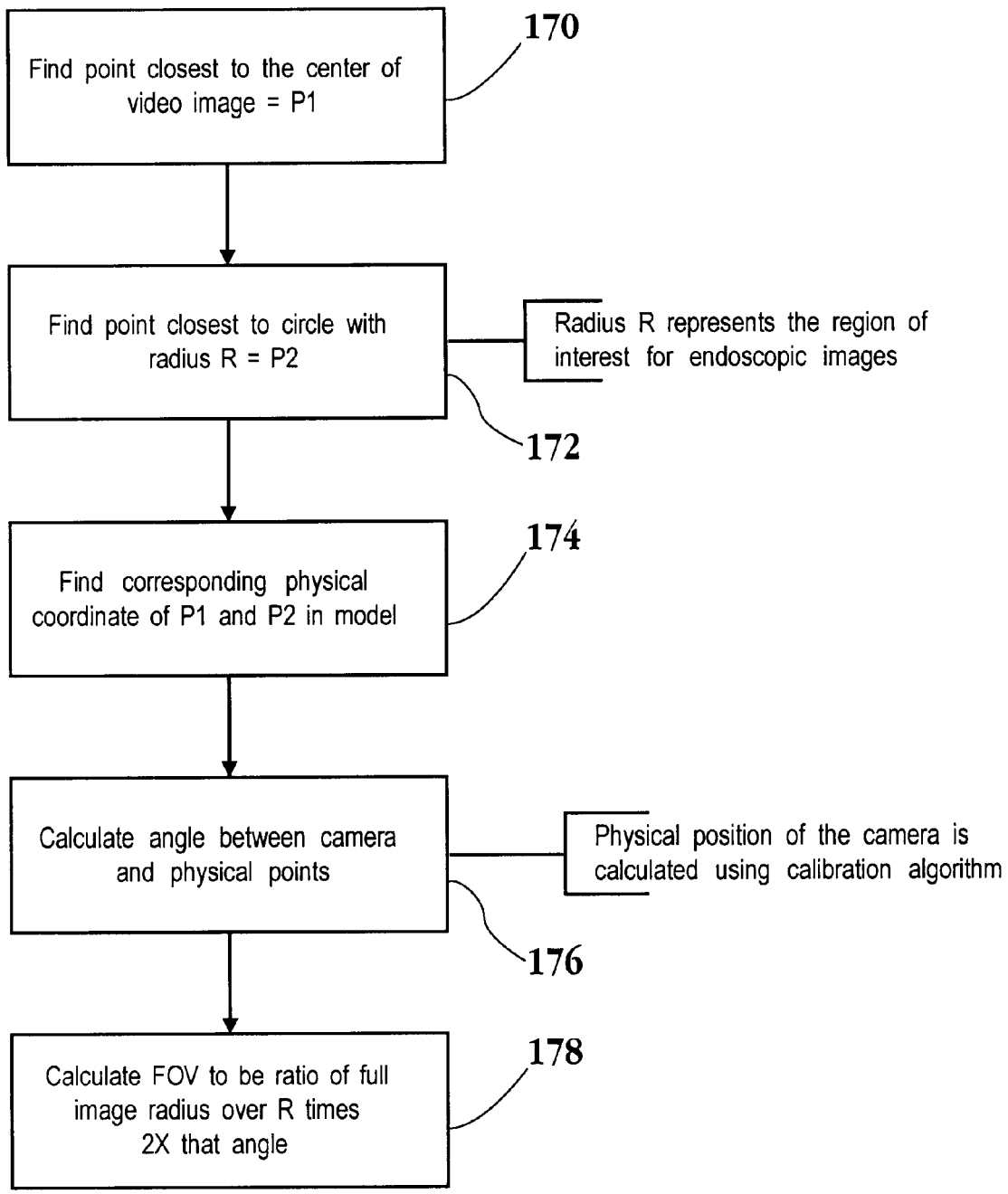
FIG. 10 is a flowchart of an additional step in the calibration operation for adjusting the FOV, if no lens distortion correction is desired.

FIG. 10 is a flow chart showing steps in the linear compensation method. As a first step, the user finds a point P1 closest to the center of the image, as at 170, then selects a circle within the image field that represents the image area of main interest for the endoscopic images, as at 172, and a second point P2 closest to the edge of the circle. For example, one may locate a point P2 whose distance from P1 is about half the total radius of the image. Using the actual coordinates of the two points physical points P1 and P2, as at 74, the calibration algorithm is used to calculate the physical position of the camera, and from this the angle between the camera and the two selected physical points, as at 176. The endoscopic field of view is then calculated as the ratio of the full image radius/R times twice the calculated angle, as at 178.

For example, assume that the initially calculated FOV is 60°, the radius of the full image is 10 inches, that of the condensed image, 5 inches, and the FOV between points P1 and P2 is 12°. The corrected or compensated FOV is thus 10/5 times 24°, or 48°. By reconstructing an image as seen by an endoscope with a 48° FOV, rather than the actual 60° FOV, the reconstructed an actual images can be closely matched in the center region of the images.

It can be appreciated from the foregoing how various objects and features of the invention are met. In both embodiments, an endoscope is readily calibrated so that (i) its position is space, as determined by tracking elements, can be accurately correlated with the three-dimensional coordinates of the lens, the view angle and twist of the endoscope, and the lens' FOV. This allows a physician, using a 3-D image reconstruction system of the type described, to view reconstructed surface of subsurface images as these would be seen by the endoscope, with the endoscope positioned and oriented at a desired view location, either outside the body or within a body orifice. The separate endoscopic and virtual images can be superimposed or viewed side-by-side, allowing the user to use virtual surface images to augment or replace endoscopic images, when the endoscope lens is clouded or blocked, and to "see beyond" an actual endoscopic view with subsurface views, e.g., perspective views as would be seen by the endoscope through x-ray vision. Further, both embodiments allow for lens distortion correction, to more accurately fit endoscopic and virtual views, particularly at the center region of the field of view.

In addition, the second embodiment provides several unique advantages which facilitate and speed up the calibration process. The method is rapid and requires little of no user input, e.g., for image matching, in order to determine all six lens coordinates, view vector, FOV, and lens distortion effects.

Because the camera-calibration algorithm employed is able to find all three (x,y,z) coordinates of the endoscope lens, and all three rotational coordinates of the endoscope, the endoscope does not have to be placed in a holder, e.g., holder cavity or cradle, that constrains two of its rotational coordinates (if the endoscope view vector is aligned with the shaft axis) or to be placed against a spot in the holder that constrains its z position. Thus, the user can simply hold the endoscope in one hand, the holder in the other, and bring the two into a desired view relationship, for initiating the calibration process.

Correcting for lens distortion effects, particularly in the central region of the image is readily accomplished by using FOV adjustments from the algorithm at full view and a reduced-field view.

Although the invention has been described with respect to various embodiments, it will be apparent to those skilled in the art in light of the foregoing description that many further alternatives, modifications and variations are possible. The invention described herein is intended to embrace all such alternatives, modifications and variations as may fall within the spirit and scope of the appended claims.

What is claimed:

1. Apparatus for use in calibrating lens position and field of view in an endoscope having an elongate shaft and a distal-end lens, comprising:

a plurality of tracking elements mounted at fixed positions on the endoscope's shaft, a holder having a guide in which the endoscope can be received to align the endoscope shaft in the holder and position the endoscope lens for viewing a three-dimensional object or pattern contained at a target area in the holder, positional elements mounted on the holder at known positions with respect to the guide and three-dimensional object or pattern, a sensing device for sensing the tracking and positional elements, a display device, and a processor operably connected to the sensing device and the display device for carrying out the following operations:

(i) determining the positions of the tracking and positional elements, with the endoscope shaft received in the holder guide, (ii) using the determined positions of the tracking and positional elements to place the endoscope and the holder in a common frame of reference, (iii) projecting on the display device, a video image of the three-dimensional holder object or pattern as seen by the endoscope with the endoscope shaft received in the holder guide, (iv) projecting a model image of the three dimensional object or pattern on the display device, representing the three dimensional object as seen from a known lens position and field of view, and (v) using information about the relative sizes, positions, and orientations of the two images to calculate the coordinates of the endoscope lens with respect to the tracking elements, and the field of the view of the lens.

2. The apparatus of claim 1, wherein using information about the relative sizes, positions, and orientations of the two images includes manually matching the endoscopic and model images, by translating, rotating and/or scaling one or both images, and from the direction and extent of such adjustments, determining the coordinates of the endoscopic lens with respect to the tracking elements, and the field of view of the lens.

3. The apparatus of claim 1, wherein information about the relative sizes, positions, and orientations said two images is used to correct for lens distortion effects.

4. The apparatus of claim 2, wherein the holder includes a stop for arresting the axial position of the endoscope in the guide at a known, selected endoscope position, and the endoscope's field of view is axially aligned with the endoscope shaft.

5. A method of calibrating lens position and field of view in an endoscope having an elongate shaft and a distal-end lens, comprising:

(a) positioning the endoscope in a holder having a guide in which the endoscope can be received to align the endoscope shaft in the holder and position the endoscope lens for viewing a three-dimensional object contained at a target area in the holder, where the endoscope has a plurality of tracking elements mounted at fixed positions on the endoscope's shaft, and the holder has positional elements mounted thereon at known positions with respect to the guide and three-dimensional object, (b) employing a sensing device to sense the positions of the tracking and positional elements, with the endoscope shaft received in said holder, (c) by means of a processor operatively connected to the sensing device and to a display device: (i) determining from input provided by the sensing device, the positions of the tracking and positional elements, with the endoscope shaft received in the holder guide, (ii) using the determined positions of the tracking and positional elements to place the endoscope and the holder in a common frame of reference, (iii) projecting on a display device, a video image of the three-dimensional holder object as seen by the endoscope with the endoscope shaft received in the holder guide, and (iv) projecting a model image of the three dimensional object on the display device, representing the three dimensional object as seen from a known lens position and field of view, and (v) using information about the relative sizes, positions, and orientations of the two images to calculate the coordinates of the endoscope lens with respect to the tracking elements, and the field of the view of the lens.

6. The method of claim 5, wherein the display device includes a split screen or two screens for displaying the two images separately on first and second screen regions, and said calculating is based on user alignment of the two images by (i) rotating one of the images to the rotational position of approximate orientation of the other image, (ii) sizing one of the images to the approximate size of the other image, (iii) superimposing the two images, and (iv) making final adjustments in image orientation and size until the two images overlap.

* * * * *